(12) United States Patent
Parham et al.

(10) Patent No.: US 10,517,628 B2
(45) Date of Patent: *Dec. 31, 2019

(54) SYSTEMS AND METHODS FOR TISSUE TREATMENT

(71) Applicant: Tenex Health, Inc., Lake Forest, CA (US)

(72) Inventors: Tate Ray Parham, Silverado, CA (US); Brad Buzea, Rancho Santa Margarita, CA (US)

(73) Assignee: Tenex Health, Inc., Lake Forest, CA (US)

( * ) Notice: Subject to any disclaimer, the term of this patent is extended or adjusted under 35 U.S.C. 154(b) by 269 days.

This patent is subject to a terminal disclaimer.

(21) Appl. No.: 15/716,278

(22) Filed: Sep. 26, 2017

(65) Prior Publication Data

US 2018/0014847 A1    Jan. 18, 2018

Related U.S. Application Data

(63) Continuation of application No. 14/866,472, filed on Sep. 25, 2015, now Pat. No. 9,770,257, which is a continuation of application No. 13/493,851, filed on Jun. 11, 2012, now Pat. No. 9,149,291.

(51) Int. Cl.
*A61B 17/32* (2006.01)

(52) U.S. Cl.
CPC ......... *A61B 17/320068* (2013.01); *A61B 2017/32007* (2017.08); *A61B 2017/320084* (2013.01); *A61B 2217/005* (2013.01); *A61B 2217/007* (2013.01)

(58) Field of Classification Search
CPC ........... A61B 17/32; A61B 17/320068; A61B 17/320092; A61B 2217/007; A61B 2017/320072; A61B 2017/320084; A61B 17/22012; A61F 9/00745; A61F 9/00736
See application file for complete search history.

(56) References Cited

U.S. PATENT DOCUMENTS

| 3,575,622 | A | 4/1971 | Nielson et al. |
| 3,589,363 | A | 6/1971 | Banko et al. |
| 3,615,366 | A | 10/1971 | Allen |
| 3,645,725 | A | 2/1972 | Denhard, Jr. et al. |
| 3,668,758 | A | 6/1972 | Krock et al. |
| 3,990,452 | A | 11/1976 | Murry et al. |
| 4,188,952 | A | 2/1980 | Loschilov et al. |

(Continued)

FOREIGN PATENT DOCUMENTS

| CN | 2402273 Y | 10/2000 |
| CN | 2774407 Y | 4/2006 |

(Continued)

OTHER PUBLICATIONS

International Application No. PCT/US2016/032055 filed on May 12, 2016.

(Continued)

*Primary Examiner* — Wade Miles
(74) *Attorney, Agent, or Firm* — K&L Gates LLP; Louis C. Cullman; Hal Gibson

(57) ABSTRACT

A system, delivery device and method delivers ultrasonic energy to a target musculoskeletal tissue site. In some embodiments, the delivery device includes a stainless steel needle joined to a horn. In some embodiments, the stainless steel needle is joined to the horn using a heating process or a brazing process.

19 Claims, 12 Drawing Sheets

(56) References Cited

U.S. PATENT DOCUMENTS

| | | |
|---|---|---|
| 4,428,748 A | 1/1984 | Peyman et al. |
| 4,515,583 A | 5/1985 | Sorich |
| 4,531,934 A | 7/1985 | Kossovsky et al. |
| 4,750,902 A | 6/1988 | Wuchinich et al. |
| 4,827,911 A | 5/1989 | Broadwin et al. |
| 4,867,141 A | 9/1989 | Nakada et al. |
| 4,870,953 A | 10/1989 | Don Michael et al. |
| 4,920,954 A | 5/1990 | Alliger et al. |
| 4,979,952 A | 12/1990 | Kubota et al. |
| 5,038,756 A | 8/1991 | Kepley |
| 5,042,461 A | 8/1991 | Inoue et al. |
| 5,108,411 A | 4/1992 | McKenzie |
| 5,139,509 A | 8/1992 | Fischer et al. |
| 5,176,677 A | 1/1993 | Wuchinich |
| 5,267,954 A | 12/1993 | Nita |
| 5,275,607 A | 1/1994 | Lo et al. |
| 5,344,395 A | 9/1994 | Whalen et al. |
| 5,403,276 A | 4/1995 | Schechter et al. |
| 5,413,556 A | 5/1995 | Whittingham |
| 5,417,654 A | 5/1995 | Kelman |
| 5,480,379 A | 1/1996 | La Rosa |
| 5,514,086 A | 5/1996 | Parisi et al. |
| 5,520,633 A | 5/1996 | Crostin |
| 5,562,609 A | 10/1996 | Brumbach |
| 5,580,347 A | 12/1996 | Reimels |
| 5,626,563 A | 5/1997 | Dodge et al. |
| 5,683,406 A | 11/1997 | Altobelli et al. |
| 5,814,016 A | 9/1998 | Valley et al. |
| 5,897,524 A | 4/1999 | Wortrich et al. |
| 5,910,110 A | 6/1999 | Bastable |
| 5,911,700 A | 6/1999 | Mozsary et al. |
| 5,935,096 A | 8/1999 | Barrett |
| D418,916 S | 1/2000 | Bastable |
| 6,033,375 A | 3/2000 | Brumbach |
| 6,077,285 A | 6/2000 | Boukhny |
| 6,090,123 A | 7/2000 | Culp et al. |
| 6,102,046 A | 8/2000 | Weinstein et al. |
| 6,139,518 A | 10/2000 | Mozsary et al. |
| 6,206,014 B1 | 3/2001 | Cameron, III et al. |
| 6,214,017 B1 | 4/2001 | Stoddard et al. |
| 6,234,993 B1 | 5/2001 | Terpilowski et al. |
| 6,270,471 B1 | 8/2001 | Hechel et al. |
| 6,311,084 B1 | 10/2001 | Cormack et al. |
| 6,379,351 B1 | 4/2002 | Thapliyal et al. |
| 6,402,769 B1 | 6/2002 | Boukhny |
| 6,437,266 B1 | 8/2002 | Pannenborg et al. |
| 6,461,301 B2 | 10/2002 | Smith |
| 6,524,251 B2 | 2/2003 | Rabiner et al. |
| 6,551,337 B1 | 4/2003 | Rabiner et al. |
| 6,562,054 B1 | 5/2003 | Weber et al. |
| 6,623,444 B2 | 9/2003 | Babaev |
| 6,660,013 B2 | 12/2003 | Rabiner et al. |
| 6,695,781 B2 | 2/2004 | Rabiner et al. |
| 6,695,782 B2 | 2/2004 | Ranucci et al. |
| 6,964,647 B1 | 11/2005 | Babaev |
| 6,980,419 B2 | 12/2005 | Smith et al. |
| 7,077,820 B1 | 7/2006 | Kadziauskas et al. |
| 7,270,656 B2 | 9/2007 | Gowda et al. |
| 7,507,212 B2 | 3/2009 | Tsuchiya et al. |
| 7,845,235 B2 | 12/2010 | Sandu et al. |
| 7,850,707 B2 | 12/2010 | Yaguchi et al. |
| 8,025,672 B2 | 9/2011 | Novak et al. |
| 8,052,701 B1 | 11/2011 | Cox et al. |
| 8,070,711 B2 | 12/2011 | Bassinger et al. |
| 8,075,503 B2 | 12/2011 | Jaeb |
| 8,303,505 B2 | 11/2012 | Webler et al. |
| 8,382,782 B2 | 2/2013 | Robertson et al. |
| 9,149,291 B2 | 10/2015 | Parham et al. |
| 9,770,257 B2 | 9/2017 | Parham et al. |
| 2002/0007200 A1 | 1/2002 | Desinger |
| 2002/0068930 A1 | 6/2002 | Tasto et al. |
| 2002/0103457 A1 | 8/2002 | Fontayne et al. |
| 2002/0107538 A1 | 8/2002 | Shibata et al. |
| 2002/0156492 A1 | 10/2002 | Timm et al. |
| 2002/0183720 A1 | 12/2002 | Hill et al. |
| 2003/0158566 A1 | 8/2003 | Brett |
| 2004/0133168 A1 | 7/2004 | Salcudean et al. |
| 2004/0162546 A1 | 8/2004 | Liang et al. |
| 2004/0259483 A1 | 12/2004 | Newell |
| 2004/0267121 A1 | 12/2004 | Sarvazyan et al. |
| 2005/0101984 A1 | 5/2005 | Chanduszko et al. |
| 2005/0119613 A1 | 6/2005 | Moenning et al. |
| 2005/0209560 A1 | 9/2005 | Boukhny et al. |
| 2005/0209621 A1 | 9/2005 | Gordon et al. |
| 2005/0228288 A1 | 10/2005 | Hurst |
| 2005/0234476 A1 | 10/2005 | Whitmore et al. |
| 2006/0195106 A1 | 8/2006 | Jones et al. |
| 2006/0241450 A1 | 10/2006 | Da Silva et al. |
| 2006/0293722 A1 | 12/2006 | Slatkine et al. |
| 2007/0250041 A1 | 10/2007 | Werp |
| 2007/0255196 A1 | 11/2007 | Wuchinich |
| 2007/0276352 A1 | 11/2007 | Crocker et al. |
| 2008/0004621 A1 | 1/2008 | Dahla et al. |
| 2008/0033349 A1 | 2/2008 | Suzuki |
| 2008/0033410 A1 | 2/2008 | Rastegar et al. |
| 2008/0058775 A1 | 3/2008 | Darian et al. |
| 2008/0091182 A1 | 4/2008 | Mehta |
| 2008/0154218 A1 | 6/2008 | Gomez et al. |
| 2008/0183109 A1 | 7/2008 | Babaev |
| 2008/0195002 A1 | 8/2008 | Thompson et al. |
| 2008/0234710 A1 | 9/2008 | Neurohr et al. |
| 2009/0024076 A1 | 1/2009 | Babaev |
| 2009/0030338 A1 | 1/2009 | Crocker et al. |
| 2009/0069712 A1 | 3/2009 | Mulvihill et al. |
| 2009/0112098 A1 | 4/2009 | Vaezy et al. |
| 2009/0312693 A1 | 12/2009 | Thapliyal et al. |
| 2010/0056986 A1 | 3/2010 | Allen et al. |
| 2010/0076476 A1 | 3/2010 | To et al. |
| 2010/0211083 A1 | 8/2010 | Sauer |
| 2010/0228207 A1 | 9/2010 | Ballakur et al. |
| 2010/0312102 A1 | 12/2010 | Barnes et al. |
| 2011/0015660 A1 | 1/2011 | Wiener et al. |
| 2011/0040212 A1 | 2/2011 | Dietz et al. |
| 2011/0066174 A1 | 3/2011 | Gilbert |
| 2011/0160620 A1 | 6/2011 | Gill et al. |
| 2011/0251461 A1 | 10/2011 | Gonzalez et al. |
| 2012/0078164 A1 | 3/2012 | Mulvihill et al. |
| 2012/0083728 A1 | 4/2012 | Sorensen et al. |
| 2012/0209303 A1 | 8/2012 | Frankouser et al. |
| 2013/0096596 A1 | 4/2013 | Schafer et al. |
| 2013/0331872 A1 | 12/2013 | Parham et al. |
| 2014/0039451 A1 | 2/2014 | Bangera et al. |
| 2015/0039005 A1 | 2/2015 | Gill et al. |
| 2015/0351790 A1 | 12/2015 | Gill et al. |
| 2016/0030685 A1 | 2/2016 | Lane |
| 2016/0059043 A1 | 3/2016 | Gill et al. |
| 2016/0096040 A1 | 4/2016 | Parham |
| 2016/0331397 A1 | 11/2016 | Parham et al. |

FOREIGN PATENT DOCUMENTS

| | | |
|---|---|---|
| CN | 2879983 Y | 3/2007 |
| CN | 101332340 A | 12/2008 |
| EP | 0709077 B1 | 3/2002 |
| EP | 1634542 A1 | 3/2006 |
| WO | 2003/101308 A1 | 12/2003 |
| WO | 2004/032596 A2 | 4/2004 |
| WO | 2006/121737 A2 | 11/2006 |
| WO | 2007/143686 A2 | 12/2007 |
| WO | 2008/024894 A2 | 2/2008 |
| WO | 2008/027223 A2 | 3/2008 |
| WO | 2008/040020 A2 | 4/2008 |
| WO | 2008/118708 A2 | 10/2008 |
| WO | 2009/105628 A2 | 8/2009 |
| WO | 2011/082219 A1 | 7/2011 |
| WO | 2012/019136 A2 | 2/2012 |
| WO | 2016/036810 A1 | 3/2016 |
| WO | 2016/054563 A1 | 4/2016 |

OTHER PUBLICATIONS

International Search Report and Written Opinion issued in PCT/US2009/034659, dated Oct. 1, 2009.

(56) References Cited

OTHER PUBLICATIONS

International Search Report and Written Opinion issued in PCT/US2010/062341, dated Mar. 25, 2011.
Kowalewski et al., Issues in Vacuum Brazing, May 1, 2006, available at https://www.secowarwick.com/assets/Documents/Articles/Vacuum-Furnaces/Issues-in-vacuum-brazing-VAC.pdf.
Lin et al., Clinical Outcomes of Ultrasound-Guided Aspiration and Lavage in Calcific Tendinosis of the Shoulder. HSSJ, 3:99-105 (2007), published online 2006.
Supplementary European Search Report Issued in EP Application No. 09712545, dated Jun. 20, 2011.
Supplementary European Search Report Issued in EP Application No. 09713554.5, dated Apr. 15, 2013.
International Search Report and Written Opinion dated Dec. 28, 2015 for International Application No. PCT/US2015/053812 filed on Oct. 2, 2015.
International Search Report and Written Opinion dated Sep. 29, 2016 for International Patent Application No. PCT/US2016/032055 filed on May 12, 2016.
International Search Report and Written Opinion dated Nov. 27, 2015 for International Application No. PCT/US2015/048075 filed on Sep. 2, 2015.
Labanca et al., Piezoelectric surgery: twenty years of use. British Journal of Oral and Maxillofacial Surgery, 46:265-269 (2008).
Supplementary European Search Report Issued in EP Application No. 10841671, dated Sep. 5, 2016.
Supplementary European Search Report Issued in in EP Application No. 13805094, dated Mar. 22, 2017.
Extended European Search Report dated May 6, 2019 for European Patent Application Serial No. 15837307.6.

SYSTEMS AND METHODS FOR TISSUE TREATMENT

CROSS-REFERENCE TO RELATED APPLICATIONS

This application is a continuation of U.S. application Ser. No. 14/866,472, filed Sep. 25, 2015, now U.S. Pat. No. 9,770,257, which is a continuation of U.S. application Ser. No. 13/493,851, filed Jun. 11, 2012, now U.S. Pat. No. 9,149,291. The disclosure of each of these applications is incorporated herein by reference in its entirety.

BACKGROUND

Repetitive motion or use of particular body tissues can cause injuries or painful conditions to arise. For example, tennis elbow, or lateral epicondylalgia is a clinical syndrome in which patients experience pain at the lateral elbow. Such pain in the lateral elbow may be worsen over time and, despite adequate treatment, many patients develop chronic symptoms and eventually become candidates for surgical treatment.

A number of surgical procedures have been described to treat chronic tendonosis or fasciitis affecting any region in the body. Particular open techniques typically require open surgical dissection down to the pathological tissue and therefore necessitate repair of the surgically compromised normal tissue. Some arthroscopic techniques can be slightly less invasive, but these arthroscopic elbow techniques have been associated with neurological complications and may require the use of a high-cost operating suite and associated personnel. Various percutaneous techniques have been described which release, ablate or resect the pathological tissue. These percutaneous techniques, however, generally require a noticeable skin incision, some surgical dissection, and the afore-mentioned use of a high-cost operating suite and supportive equipment and personnel.

Accordingly, a need exists for the further development of systems for minimally invasive tissue treatment.

SUMMARY

In some embodiments, the system, delivery device and method delivers ultrasonic energy to a target musculoskeletal tissue site. In some embodiments, the delivery device includes a stainless steel needle joined to a horn. The stainless steel needle may be joined to the horn using a heating process or a brazing process.

Some embodiments relate to a system for musculoskeletal tissue treatment under ultrasonic guidance. The system may include a delivery device and a controller configured to deliver a power signal to the delivery device. The delivery device may include a housing portion, a transducer, and a stack assembly.

In some embodiments, the housing and the stack assembly may define portions of an aspiration conduit and an irrigation conduit.

In some embodiments, the delivery device includes a horn assembly which receives ultrasonic energy and delivers the ultrasonic energy to the musculoskeletal tissue site.

Additional features and advantages are described herein, and will be apparent from the following Detailed Description and figures.

DETAILED DESCRIPTION

Various embodiments described herein provide systems for accessing and treating target body tissue (e.g., tendon tissue, ligament tissue, muscle tissue, bony tissue, and the like) under guidance of ultrasound imaging equipment. In some embodiments, the system includes a delivery device having a stainless steel type needle brazed to a horn using a heating process or brazing process. The brazing or heating processes described herein may allow for an increase in the length of the stainless steel type needles which may be used by a delivery device for accessing and treating target body tissue.

Figure 1:
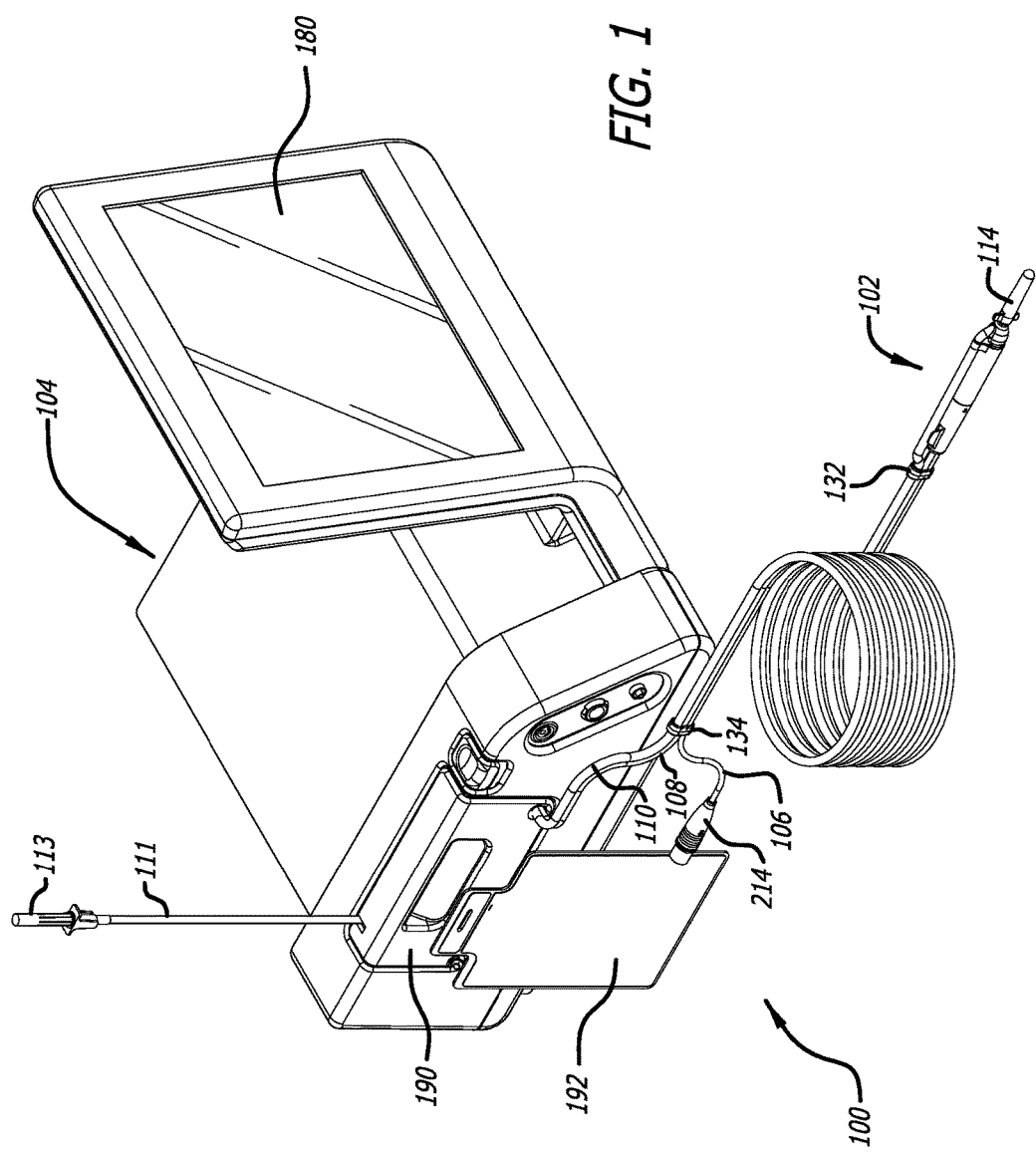
FIG. 1 is a perspective view of one example embodiment of the system disclosed herein.

FIG. 1 illustrates an example system according to an example embodiment of the present disclosure which is configured to percutaneously access and act upon target tissue while helping reduce collateral trauma. In some example embodiments, the minimally-invasive ultrasonic nature of system 100 increases the accuracy of removing diseased tissue when compared to surgical procedures which include surgical dissections of healthy tissue. In some embodiments, the percutaneous, minimally-invasive nature of system 100 facilitates treatment of a patient in an office setting under local anesthesia. Treatment in an office setting is advantageous in several respects, for example, including patient comfort and convenience and avoiding costs associated with operating room time and general anesthesia.

Figure 14:
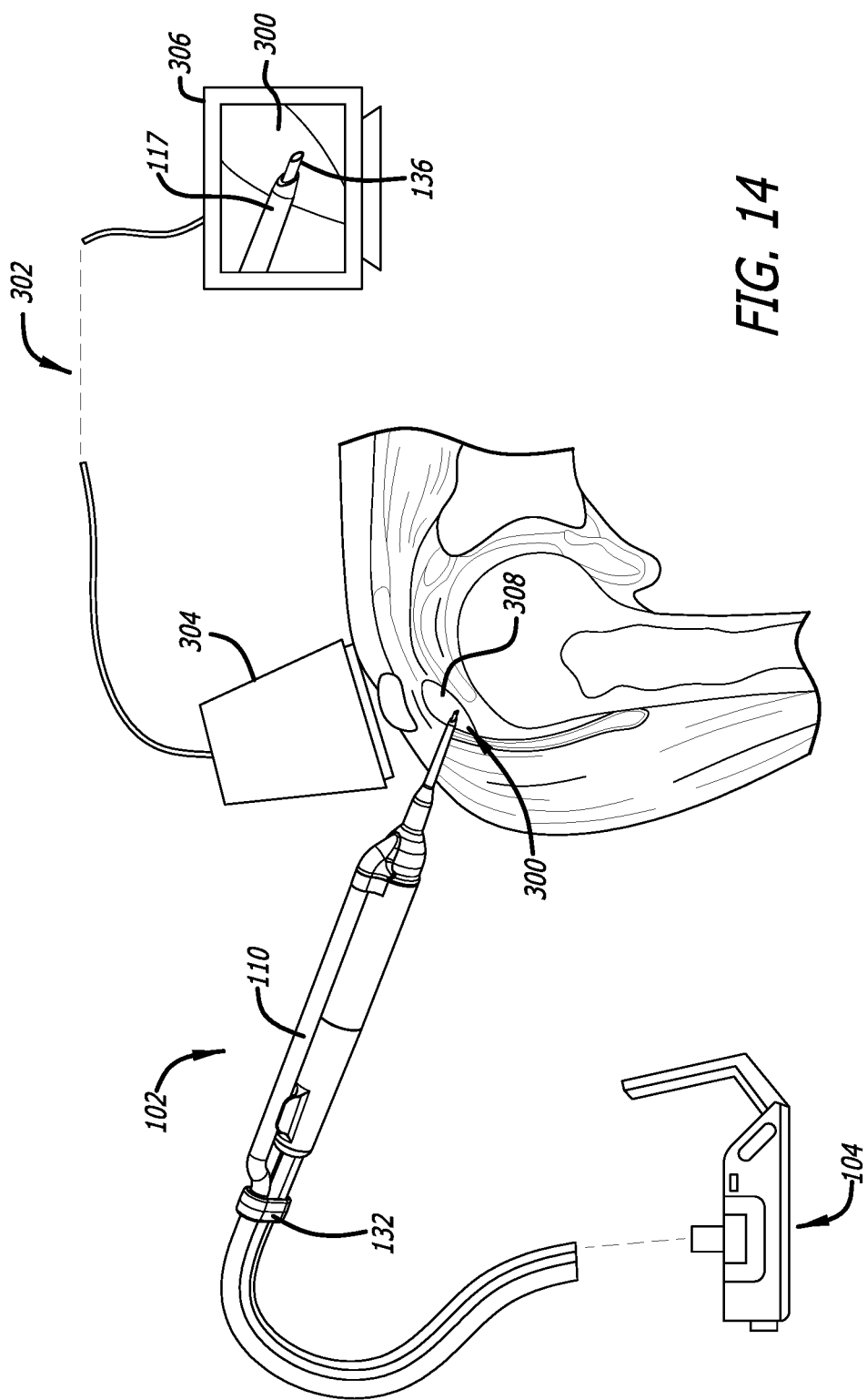
FIG. 14 illustrates a diagrammatic view of one example of the system being used in conjunction with ultrasound imaging system to deliver ultrasonic energy to a target musculoskeletal tissue site under ultrasonic imaging.

In some embodiments, as best illustrated in FIGS. 1 and 14, system 100 includes delivery device 102 and controller 104 which is operatively connected delivery device 102.

In some embodiments, as illustrated in FIG. 1, delivery device 102 is operatively connected to controller 104 via power line 106, vacuum line 108 and irrigation line 110.

Power line 106 may connected to controller 104 via a wired connection as shown in FIG. 1. In another embodiment, controller 104 may be configured to communicate with delivery device 102 via a wireless communication or a combination of a wired communication and a wireless communication.

Figure 2:
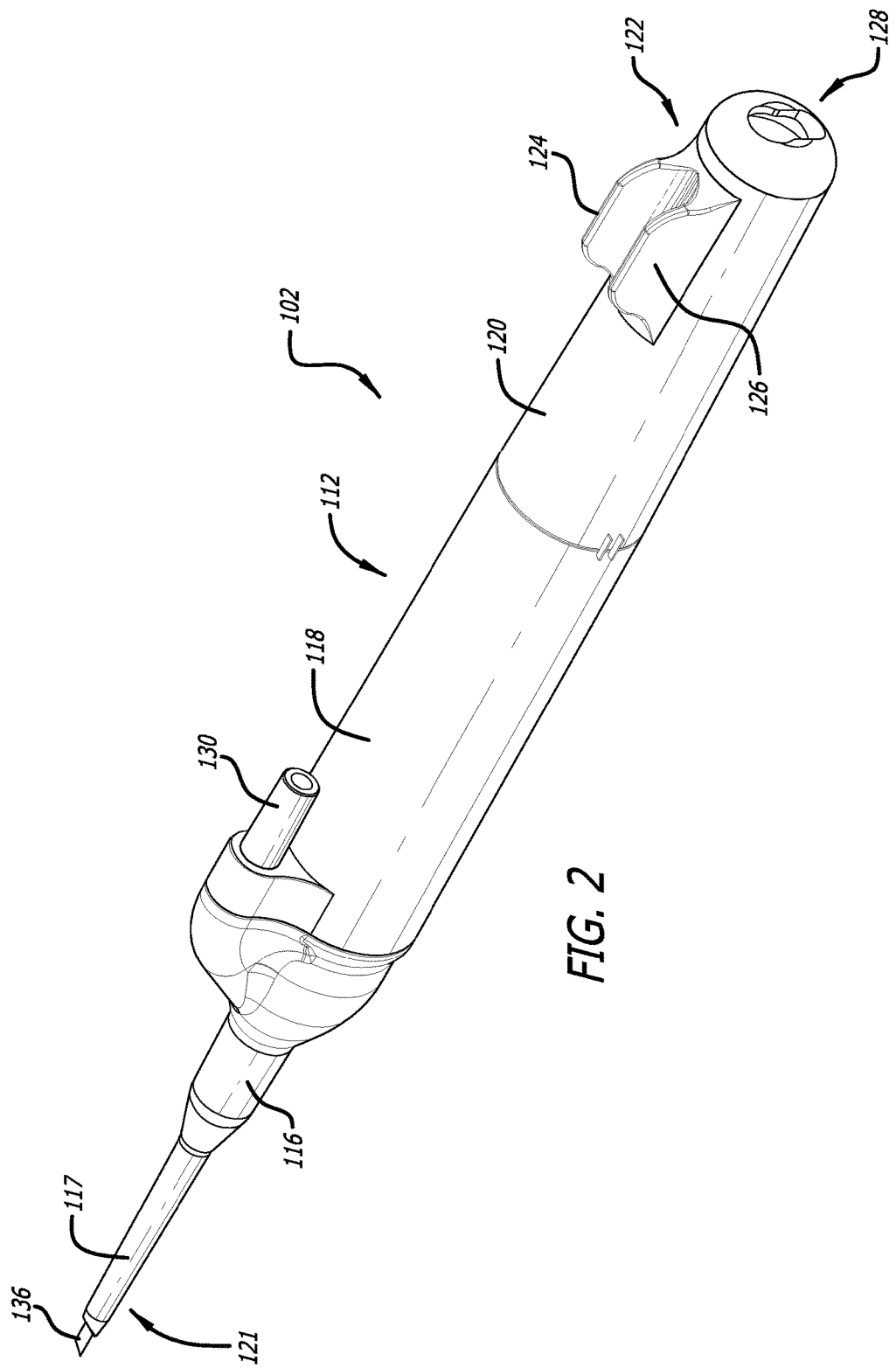
FIG. 2 is a perspective view of one example embodiment of the delivery device disclosed herein, illustrating an example extension and an example tab.
Figure 3:
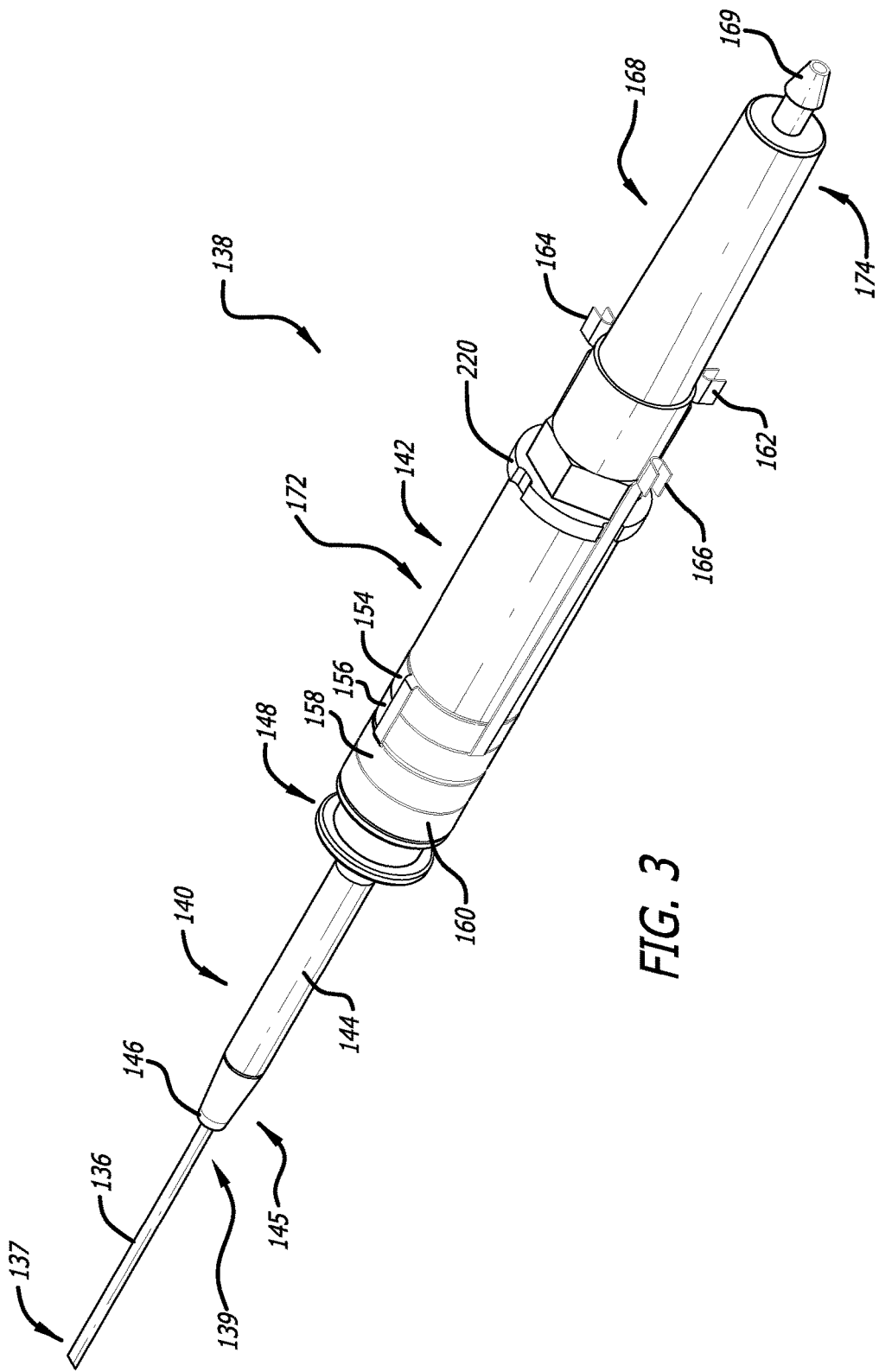
FIG. 3 is a perspective view of one example embodiment of the stack assembly, illustrating the horn assembly, the crystal stack assembly and the compressor.

In some embodiments, delivery device 102 is configured to transmit ultrasonic energy to a percutaneous musculoskeletal site at a pre-tuned frequency selected to debride musculoskeletal tissue. As best illustrated in FIGS. 1 to 3, in some embodiments, delivery device 102 includes: (a) housing 112; and (b) stack assembly 138. In some embodiments, delivery device includes cap 114.

In some embodiments, housing 112 includes at least two separate portions. For example, as illustrated in FIG. 2, housing 112 include includes: (a) nose portion 116; (b) body portion 118; and (c) tail portion 120.

Figure 10:
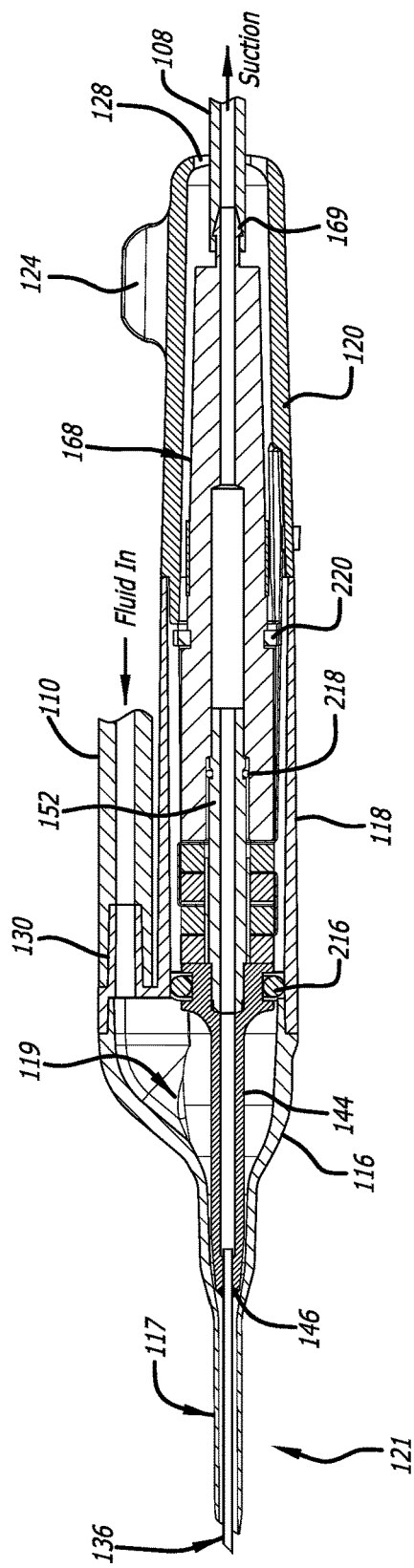
FIG. 10 is a cross-sectional view of one example of the delivery device, illustrating the irrigation conduit and the vacuum conduit.

In some embodiments, as discussed in more detail below, the housing includes a portion configured to form part of an irrigation conduit. For example, as best illustrated in FIGS. 2 and 10, nose portion 116 includes portion or sleeve 117. In this example, sleeve 117 defines an inner lumen or channel which forms part of an irrigation conduit.

In some embodiments, sleeve 117 has an insertion portion 121 which extends to a terminal end and is adapted for percutaneous insertion.

Insertion portion 121 of sleeve 117 may be any suitable size. In some example embodiments, insertion portion 121 has a size of about twelve gauge or less, about twelve gauge to about twenty-five gauge, or about fourteen gauge to about twenty-two gauge.

Insertion portion 121 may have a lateral width of any suitable size. In some example embodiments, insertion portion 121 has a lateral width of about 2.5 mm or less, about 2.2 mm to about 0.4 mm, or about 2.1 mm to about 0.5 mm.

The length of insertion portion 121 may be any suitable size. In some example embodiments, the length of insertion portion 121 is about three inches to about 0.25 inches, about 2.7 inches to about 0.5 inches, or about 2.5 inches to about 1.0 inch.

In some embodiments, the terminal end of insertion portion 121 is formed with a sharp angle or in other embodiments is squared off.

Insertion portion 121 may leave the exposed portion of needle 136 at any suitable length. In some embodiments, insertion portion 121 may leave the exposed portion of needle 136 at a length of about 10 mm or less, for example between from 2 mm to about 10 mm.

In some embodiments, as best illustrated in FIGS. 2 and 10, sleeve 117 may be integrally formed as part of nose portion 116. In another embodiment, needle sleeve 117 is separate from and connects to nose portion 116.

Sleeve 117 may be formed of an echogenic, biocompatible material suitable for dampening products of ultrasonic energy (e.g., heat and vibration). In some embodiments, sleeve 117 is coated with an echogenic material. In some embodiments, sleeve 117 is formed of a material exhibiting a differential echogenicity to that of needle 136. In such embodiments, both needle 136 and sleeve 117 facilitate ultrasonic imaging and separate identification during percutaneous insertion.

In some embodiments, nose portion 116 is configured to function as a guide for needle 136 during ultrasonic vibration.

In some embodiments, as illustrated in FIG. 10 and discussed in more detail below, nose cone portion 116 defines channel 119 for enabling and/or directing fluid flow into an incision site. The fluid flow may remove any heat buildup due to friction.

In some embodiments, to prevent air from being delivered to a musculoskeletal tissue site from the irrigation conduit, system 100 is configured to evacuate air from the irrigation conduit. Nose portion 116 may be formed from substantially clear material which allows a user to determine whether any air bubbles exist in the irrigation conduit.

In some embodiments, housing 112 may define a portion to facilitate a connection to irrigation line 110. For example, as best illustrated in FIG. 2, body portion 118 defines extension 130 which enables delivery device 102 to connect to irrigation line 110. In some embodiments, as best illustrated in FIGS. 2 and 10, extension 130 defines a hollow lumen having an inlet.

Extension 130 may be configured such that irrigation line 110 slides over the outer surface of extension 130. The outside surface of extension 130 may have a luer type taper on the outside surface of extension 130 which is configured to connect to irrigation line 110.

Extension 130 may have any suitable shaped cross section, such as, for example, a cylindrical cross section or a substantially square-shaped cross section. In this example, extension 130 forms part of the irrigation conduit. In another example, extension 130 may have a barb fitting to connect to irrigation line 110.

In some embodiments, extension 130 may be referred to as a tube fitting.

As illustrated in FIGS. 2 and 10 and discussed in more detail below, in some embodiments, tail portion 120 defines opening 128 which allows vacuum line 108 and power line 106 to connect to delivery device 102.

In some embodiments, housing 112 has a substantially cylindrical-shaped cross section. In other embodiments, housing 112 may a different shaped cross section, such as, for example a substantially square-shaped cross section.

The above-described separate portions of housing 112 may be configured to connect to each other using any suitable method. For example, in some embodiments, using glue, nose portion 116 may be configured to mate with and connect to a first end of body portion 118, and tail portion 120 may be configured to mate with and connect to the opposite end of body portion 118.

Housing 112 may be formed of any suitable material including molded plastic and/or Acrylonitrile Butadiene Styrene.

In an embodiment where housing 112 is designed to include separate portions such as the portions described above, this design may provide a cost effective method for producing a low cost ultrasonic hand piece.

Cap 114 may be configured to be removably connected to housing 112. For example, FIG. 1 illustrates cap 114 being connected to nose portion 116, and FIG. 2 illustrates cap 114 being removed from nose portion 116. In some embodiments, cap 114 is configured to removably connect to nose portion 116 by employing a luer taper interface.

In some embodiments, cap 114 is configured to seal the fluid system of system 100. Such a configuration enables system 100 to be primed and prepared for surgery.

In some embodiments, as best illustrated in FIGS. 3 to 9B, stack assembly 138 includes: (a) horn assembly 140; (b) crystal stack assembly 142; and (c) compressor 168.

Figure 7:
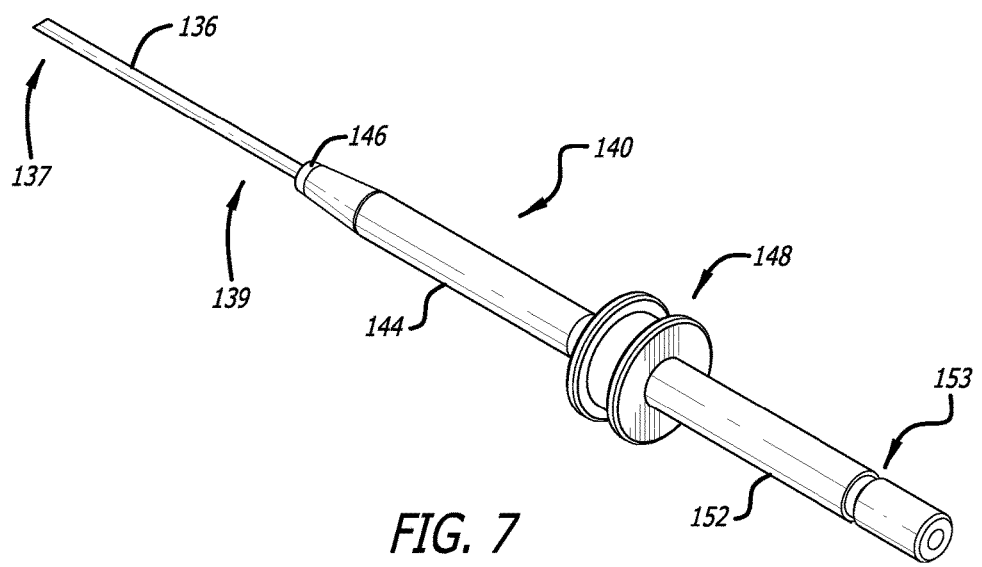
FIG. 7 is a perspective view of one example of the horn assembly, illustrating the horn assembly being connected to the mounting member.

In some embodiments, delivery device 102 includes a mounting member. For example, as illustrated in FIGS. 7 and 10, delivery device 102 includes mounting member 152.

Figure 6:
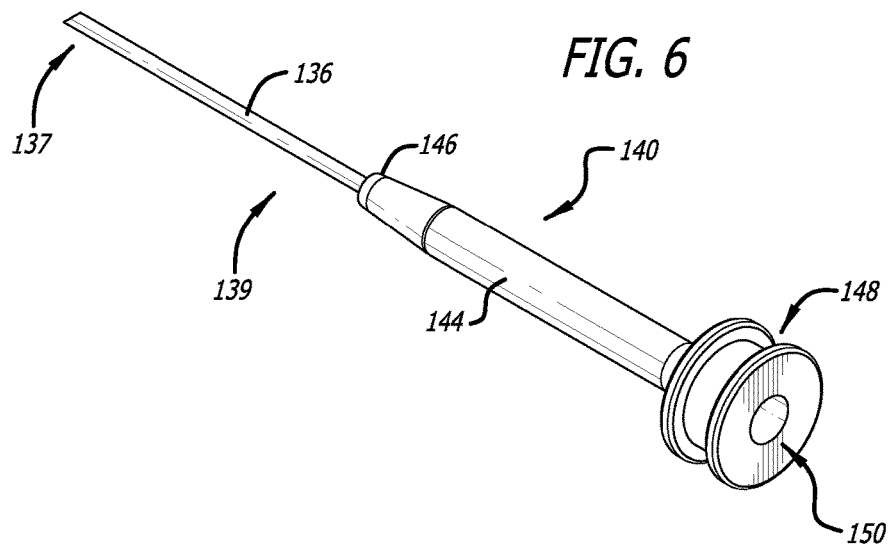
FIG. 6 is a perspective view of one example of the horn assembly, illustrating the horn having an opening for connecting to the mounting member.

In some embodiments, horn assembly 140 is configured to connect to mounting member 152. For example, as illustrated in FIG. 6, in one embodiment, opening 150 may define a threaded portion which is configured to mate with and connect to a threaded portion of mounting member 152. FIG. 7 illustrates one example of mounting member 152 being connected to horn assembly 140. It should be appreciated that horn assembly 140 may connect to mounting member 152 in any suitable manner.

In some embodiments, horn assembly 140 includes mounting member 152. That is, in these embodiments, mounting member 152 is not a separate component of horn assembly 152, but rather is formed as a single, integral component of horn assembly 152. For example, horn 144 and mounting member may be formed as a single component.

In some embodiments, horn assembly 140 includes: (a) needle 136; and (b) horn 144.

In some embodiments, needle 136 is a generally hollow tubular member which defines a lumen. As illustrated in FIGS. 3, 6, 7 and 10, needle 136 may have distal portion 137 and proximal portion 139.

Distal portion 139 is preferably adapted for percutaneous insertion. Distal portion 139 may be formed at a sharp angle or may be squared off. In some embodiments, distal portion 139 may have serrated edges or other surface features for enhancing ultrasonic debridement.

In some embodiments, needle 136 is covered or coated with echogenic material.

Distal portion 137 may have any suitable size. In some example embodiments, distal portion 137 has a size of about 12 gauge or less, about 12 gauge to about 25 gauge, or about 14 gauge to about 22 gauge.

Distal portion 137 has a lateral width of any suitable size. In some example embodiments, display portion 137 has a lateral width of about 2.5 mm or less, about 2.2 mm to about 0.4 mm, or about 2.1 mm to about 0.5 mm.

The length of distal portion 137 may be any suitable size. In some example embodiments, the length of distal portion 137 is about three inches to about 0.25 inches, about 2.7 inches to about 0.5 inches, or about 2.5 inches to about one inch.

In some embodiments, needle 136 is formed of an echogenic, biocompatible material suitable for conveying ultrasonic energy. For example, needle 136 may be formed of a stainless steel alloy. In some embodiments, needle 136 may include a stainless steel hypodermic needle. In some embodiments, needle 136 may be formed from a 174 precipitant hardened stainless steal. In some embodiments, needle 136 includes a heat hardened stainless steal. In some embodiments, needle 136 includes a work hardened stainless steal, such as 300 stainless steal.

In some embodiments, needle 136 may have a forty-five degree bevel to facilitate insertion into the surgical site.

In some embodiments, as best illustrated in FIGS. 2 and 10, sleeve 92 and needle 136 are positioned such that needle 136 has a covered portion and an exposed portion.

In some embodiments, sleeve 117 may be configured to reduce unwanted, collateral transmission of heat, ultrasonic energy, or other byproducts of the ultrasonic energy being conveyed along the covered portion of needle 136. Sleeve 117 may reduce or eliminates damage to non-target body tissues as a result of unwanted transmission of ultrasonic energy.

In operation, needle 136 vibrates at the surgery site and breaks up certain tissue up such as scarred tendon tissue, osteophytes, and calcifications. Needle 136 may configured to direct the aspiration flow from the bore of needle 136 back to collector 192.

In some embodiments, horn 144 is configured to compress piezoelectric crystals and amplify ultrasonic vibration.

Figure 4:
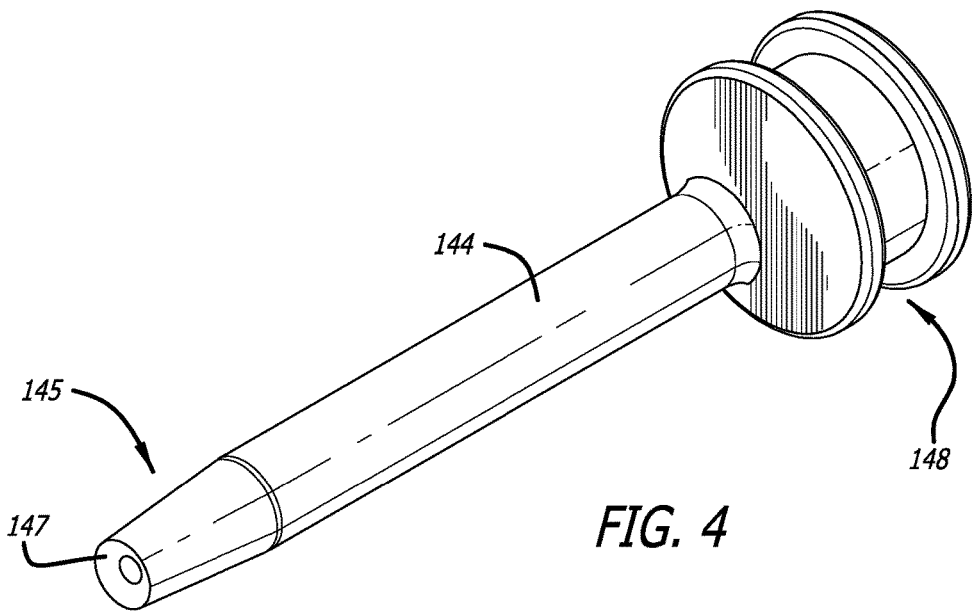
FIG. 4 is an enlarged perspective view of one example of the horn, illustrating the horn having a groove portion and a slanted tip portion.
Figure 5:
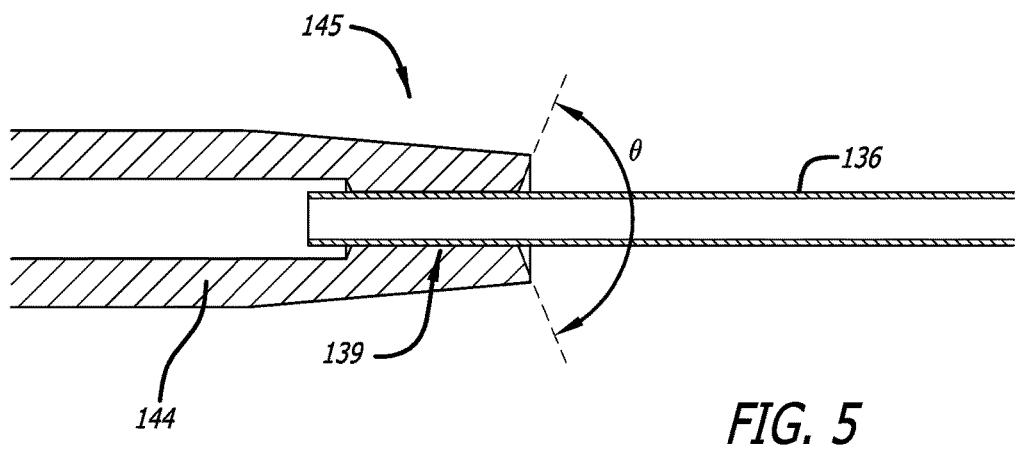
FIG. 5 is a longitudinal section of a portion of the horn assembly, illustrating the slanted tip portion having an angle of about 135°.

In some embodiments, horn 140 may have a tip portion configured to enable or allow for a more durable connection between horn 140 and needle 136. For example, as illustrated in FIGS. 4 and 5, horn 140 has tip portion 145. In this example, tip portion 145 defines slant portion 147 having an angle ("θ"). In one example, θ is about 135°. Slant portion 147 enables for a more durable connection between horn 140 and needle 136. In this example, slant portion 147 slants inwardly. In this example, this cupped-shaped portion allows for the brazing material to pool into said portion.

In some embodiments, horn 144 defines an opening to connect to other components of delivery device 102. For example, as illustrated in FIG. 6, horn 140 defines opening 150 which enables horn 140 to receive mounting member 152. In one example, mounting member 152 connects to horn 144 via a threaded connection. It should be appreciated that mounting member 152 may connect to horn 144 in any manner.

In some embodiments, as described above, horn assembly 140 includes horn 144 and needle 136. In other embodiments, horn assembly 140 includes horn 144, needle 136 and mounting member 152. In one embodiment, horn 144 and mounting member 152 are formed as a single integral component.

Horn 144 may be made of a metal such as stainless steel. In some embodiments, both horn 144 and needle 36 are made of only stainless steal.

In some embodiments, mounting member 152 defines a bore or lumen which forms a portion of the vacuum conduit and directs aspiration flow from horn assembly 140 to a lumen defined by compressor 168.

In some embodiments, mounting member 152 is made from titanium, which may allow for stack assembly 138 to resonate at a proper frequency (e.g., between 25 KHz and 30 KHz).

Mounting member 152 may be frictionally fit, adhered, welded, or otherwise secured within housing 112.

In some embodiments, crystal stack assembly 142 is disposed around mounting member 152.

In some embodiments, using a material (e.g., a brazing material), needle 136 is connected to horn 140 by employing a brazing process or a heating process. During the brazing process, the brazing material melts the brazing material to cause needle 136 to join together with horn 144 to form a single contiguous horn assembly. The melting temperature of the brazing material alloy is preferably low enough such that needle 136 will not anneal during the brazing process. The melting temperature of the brazing material facilitates fixing the needle to the horn.

During the brazing process, needle 136 may be in a condition that can be affected by an elevated temperature. If needle 136 anneals during a brazing process or heating process, then strength of needle 136 is reduced, and needle 136 will likely break during ultrasonic vibration. Because needle 136 cannot anneal, needle 136 cannot be brazed to horn 144 in a vacuum braze environment.

In some embodiments, using the brazing process described herein, needle 136 may be brazed to horn 144 such that needle 136 will not annealed during the brazing or heating process.

For example, in one example, needle 136 and horn 144 may be formed of stainless steel. In this example, needle 136 and horn 144 may be joined together using an acid flux and inert gas (e.g., nitrogen) to facilitate the braze material flow during the brazing process. In some embodiments, needle 136 is brazed to horn 144 using an induction brazing machine which employs heat generated from an electromagnetic field created by the alternating current from an induction coil. In some embodiments, the braze joint is protected against oxidation by placing a tube over the braze joint. After the tube is placed over the brazed joint, gas may be added. In some embodiments, an additive (e.g., acid flux) may be used to break surface tension of the metal of the needle and the horn.

The brazing or heating processes described herein may increase the sizes of the stainless steel type needles which may be used by a delivery device to function properly. In certain delivery devices having certain types of stainless steel needles attached to a horn, the stainless steel needle may break based on the needle's strength. For example, where a stainless steel needle has a length of about twenty-two times the diameter of the bore diameter, it has been found that the manufacturability decreases and the costs substantially increase. Although, a titanium type needle may be used in certain situations to increase the length of the needle, a titanium type needle is significantly more expensive than a stainless steel type needle. Using the brazing or heating procedure described herein, delivery device 102 may include a stainless steel needle having a length of about one thousand times the diameter of the bore. Such a configuration may provide for reduced cost of delivery device 102 by eliminating components typically used in the construction of a delivery device (e.g., a titanium needle).

In some embodiments, the brazing material may include an alloy, nickel, silver, copper and/or a silver based alloy perform.

In some embodiments, the brazing material is supplied as a preformed donut shape, similar to braze ring 146 illustrated in FIGS. 3, 6, 7 and 10. In some embodiments, the brazing material to supplied as a wire which may have, for example, a 1/32" diameter.

The brazing material may have a high density. In some embodiments, the brazing material has a higher density than needle 136 and horn 144. In these embodiments, horn 144 may be tuned to different resonant frequencies based on the volume of braze material applied. For example, in one embodiment, system 100 includes a 27 KHz drive signal generator. In this example, the mechanical system may have to resonate between 25 KHz and 29 KHz to function properly. If it is determined that stack assembly 138 is resonating at 31 KHz, stack assembly 138 will not function properly. In this example, adding more brazing material can reduce the resonating frequency of stack assembly 138, and therefore enable stack assembly 138 to function properly.

In some embodiments, needle 136 is a fully hardened hypodermic needle which is brazed to horn 144.

In some embodiments, needle 136 is connected to horn 144 using a brazing material including silver because silver has a melting point below the annealing point of stainless steal.

In some embodiments, needle 136 is not directly connected to horn 144. For example, needle 136 may be connected to a component which is connected to horn 144. In these embodiments, needle 136 may be described as being operatively connected to horn 144. However, it should be understood that where needle 136 is directly connected to horn 144, needle 136 may be described as being operatively connected to horn 144 also.

In one example embodiment, by brazing needle 136 horn 144, the system described herein may function properly with needle 136 having a length of threes inches and a bore size of 0.035 inches.

Figure 8:
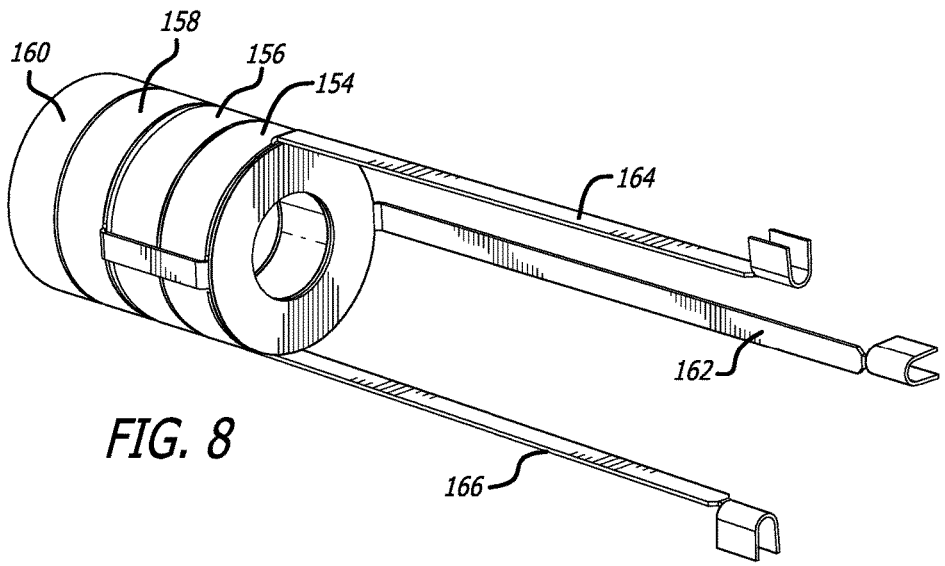
FIG. 8 is a perspective view of one example of the crystal stack assembly, illustrating the crystal stack assembly having piezoelectric crystals and electrodes.
Figure 9A:
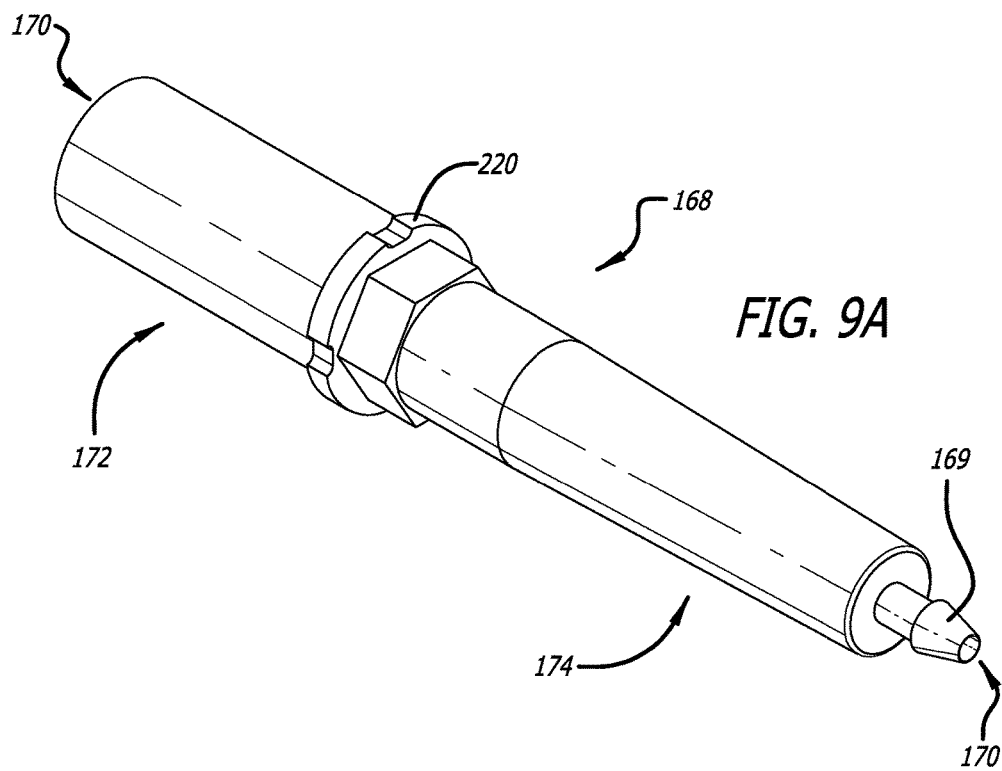
FIGS. 9A and 9B are perspective views of one example of the compressor, illustrating the compressor defining a lumen and having a barbed fitting.
Figure 9B:
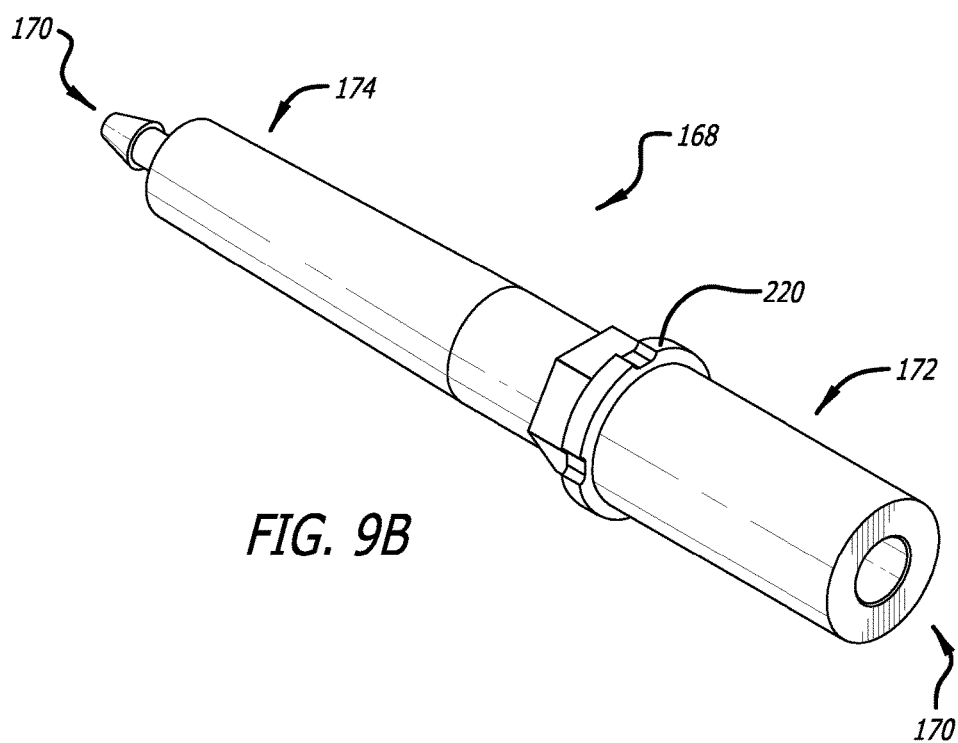

In some embodiments, crystal stack assembly 142 includes a transducer which is configured to generate ultrasonic energy based on a power signal. For example, as illustrated in FIG. 8, crystal stack assembly 142 includes a transducer which is configured to generate ultrasonic energy based on a power signal which is provided from controller 102. The ultrasonic energy may be applied in a pulsed fashion or continuous fashion.

In some embodiments, the transducer includes piezoelectric crystals. For example, as illustrated in FIG. 8, the transducer includes: (a) first piezoelectric crystal 154; (b) second piezoelectric crystal 156; (c) third piezoelectric crystal 158; and (d) fourth piezoelectric crystal 160. In this example, the transducer is operatively connected to: (a) first electrode 162; (b) second electrode 164; and (c) third electrode 166.

In some embodiments, the transducer is mounted to mounting member 152 such that ultrasonic energy generated by the transducer is transferred to horn assembly 140.

The transducer may be configured to generate longitudinal vibration, transverse vibration, or combinations thereof at desired frequencies. For example, the number and configuration of the piezoelectric crystals may be varied to modify the ultrasonic frequency used for tissue treatment.

As illustrated in FIG. 8, in some embodiments, crystal stack assembly 142 may include four piezoelectric crystals. In other embodiments, crystal stack assembly may include at least two piezoelectric crystals.

In some embodiments, as illustrated in FIG. 8, the piezoelectric crystals may be donut-shaped.

In some embodiments, as illustrated in FIGS. 8 and 10, the piezoelectric crystals may be configured to receive mounting member and be positioned over mounting member 152.

In some embodiments, the piezoelectric crystals and electrodes are compressed between horn assembly 140 and compressor 168.

The piezoelectric crystals may be assembled such that the polarizations are aligned.

In some embodiments, portions of the electrodes are sandwiched between the piezoelectric crystals. In some embodiments, the electrodes supply the electric charge to cause these crystals to vibrate.

In some embodiments, as best illustrated in FIG. 8, the ends of electrodes 162, 164 and 166 have a crimping feature which allows for crimping wires to create an electromechanical connection. This type of connection is typically a solder connection. Such a configuration allows for assembly in a clean room without having soldering fumes or acid flux clean up.

In some embodiments, the electrodes include a positive electrode which has a portion that jumps between the positive polarities of the crystals.

In some embodiments, the electrodes include negative electrodes which create a safety ground loop circuit.

In some embodiments, the negative electrodes are placed between the flat surfaces of the crystals. In these embodiments, the negative electrodes may contact the metal components of the stack to complete the ground circuit.

In some embodiments, compressor 168 is configured to provide compression force for crystal stack assembly 142. Compressor 168 may be torqued to a predetermined value to achieve a specific crystal compression.

As illustrated in FIGS. 3, 9A, 9B and 10, in some embodiments, compressor 168 may have first end portion 172 and second end portion 174. In some embodiments, compressor 168 defines opening or bore 170 which runs from first end portion 172 to second end portion 174. Opening 170 may be used for directing the aspiration flow to the vacuum line 108.

In some embodiments, compressor 168 may connect to mounting member 152 using any suitable connection method. In some embodiments, first end portion 172 of compressor 168 is connected to mounting member 152 via a threaded connection.

Compressor 168 may include fitting configured to connect to vacuum line 108. For example, as illustrated in FIGS. 3 and 10, compressor 168 includes barb fitting 169 which is configured to connect to vacuum line 108. In this embodiment, barb fitting 169 is integrally formed with compressor 168. In another embodiment, barb fitting is separate from and operably connects to compressor 168. Barb fitting 169 may provide an interference fit with vacuum line 108. Barb fitting 169 may provide for reduced cost of delivery device 102 by eliminating components typically used in the construction of a delivery device.

In some embodiments, compressor 168 may be referred to as a compression nut.

In some embodiments, delivery device 102 includes an irrigation conduit which enable delivery device 102 to deliver fluid to a musculoskeletal tissue site.

As illustrated in FIG. 10, in some embodiments, the irrigation conduit may be formed by portions of (a) housing 112; and (b) horn assembly 140. More specifically, in some embodiments, the irrigation conduit may formed such that fluid may be passed from the inlet of extension 130, through channel 119 of nose portion 112 and out of sleeve 117 of nose portion 116.

In some embodiments, as best illustrated in FIG. 10, needle 136 and sleeve 92 are secured relative to one another, with needle 136 disposed in the inner lumen of sleeve 92, needle 136 and sleeve 92 define a gap between them to form a portion of the irrigation conduit.

In some embodiments, an outlet from the irrigation conduit may be defined between the terminal end of sleeve 92 and needle 136. Thus, fluid passing into the irrigation conduit in a distal direction passes from the irrigation conduit with fluid generally encircling, or circumscribing the insertion portion of needle 136 and being directed toward the exposed portion of needle 136.

In some embodiments, delivery device 102 includes a vacuum conduit which enables delivery device 102 to remove detritus from the musculoskeletal tissue site.

Referring to FIG. 10, the vacuum conduit may be formed by the lumen portions of: (a) horn assembly 140; (b) mounting member 152; and (c) compressor 138. As illustrated in FIG. 10, the vacuum conduit may be formed by lumens formed in needle 136, horn 144, mounting member 152 and compressor 168.

The vacuum conduit may pass through the transducer as shown in FIG. 10.

In some embodiments, as illustrated in FIG. 10, delivery device 102 includes gasket or O-ring 216. In these embodiments, gasket 216 is configured to fit into groove portion 148 of horn 144. Such a configuration creates a seal between housing 112 and horn 144 such that fluid within the inner compartment formed by nose portion 116 is prevented from entering within body portion 118 and fluid may be delivered through the irrigation conduit.

As illustrated in FIG. 10, delivery device 102 may include gasket 216 disposed between body portion 118 and nose portion 116. In some embodiments, during assembly of delivery device 112, body portion 118 may slide over stack assembly 138 up to and engage gasket 216.

In some embodiments, as illustrated in FIG. 10, delivery device 102 may include gasket or O-ring 218 for creating a seal between mounting member 152 and compressor 168 which may prevent thread lock fluid from running into any piezoelectric crystals. In these embodiments, mounting member 152 may include groove portion 153 as best illustrated in FIG. 7. In this example, gasket 218 is configured to fit into groove portion 153.

In some embodiments, as illustrated in FIG. 10, delivery device 102 may include electrode isolator 220 configure to provide a barrier between compressor 168 and housing 12 and isolate certain electrodes (e.g., a positive electrode) from compressor 168.

Electrode isolator 220 may be configured to isolate compressor 168 from housing 112 during vibration to minimize the effect of the vibration on housing 112 by maintaining electrical and mechanical separation. Electrode isolator 220 may be formed from rubber. Electrode isolator 220 may be configured to be placed in groove 171 of compressor 12.

In some embodiments, tape made with Kapton® polyimide film may be used to electrically isolate the positive electrodes from the ground electrodes and other ground components.

In some embodiments, at each threaded junction, a thread locker is applied to prevent the threads from loosening and to prevent fluid ingress.

In some embodiments, delivery device 102 is a free floating resonator. That is, in this example, delivery device 102 is not fixed such as being fixed to the housing at the tail end. Such a configuration allows for a cost effective manufacture of the delivery device, because, for example, the housing may be formed of a molded plastic material.

In some embodiments, the seal components and vibration isolators are formed of a dampening or insulating material, such as a relatively soft polymeric material, for reducing or inhibiting proximal transmission of ultrasonic energy or other undesirable ultrasonic energy transmission. For example seal 216 and electrode isolator 220 may be formed of silicone, although a variety of materials are contemplated.

In some embodiments, system 100 may include line holders configured to hold the lines of the system together to keep the lines from twisting or knotting together. For example, as illustrated in FIG. 1, system 100 includes first holder 132 and second holder 134 which are configured to keep power line 106, vacuum line 108 and irrigation line 110 from twisting together. In one embodiment, line holders 132 and 134 are configured to slide over power line 106, vacuum line 108 and irrigation line 110. In one embodiment, line holders 132 and 134 are configured to provide a snap fit over power line 106, vacuum line 108 and irrigation line 110. In one embodiment, holders 132 and 134 are used after vacuum line 108 and irrigation line 110 have been separated for assembly.

Referring to FIG. 1, system 100 may include connector 214 which is configured to removably connect to controller 104. Connector 214 may be made of molded plastic and may include three contacts.

In some embodiments, power line 106 may include the following three conductors: (a) a first conductor for high voltage power; (b) a second conductor for a ground loop; and (c) a third conductor for providing a safety ground feedback and redundancy.

Generally, various components of delivery device 102 contemplated for tissue contact are formed of biocompatible and/or other suitable materials depending upon implementation.

As illustrated in FIG. 1, delivery device 102 may be ergonomically designed, adapted to be hand held (e.g., as a stylet) or otherwise adapted to be manually operated using a single hand. In another embodiment, delivery device 102 may be adapted to be manipulated automatically or semi-automatically (e.g., as part of a robotic system).

In some embodiments, delivery device 102 is pre-tuned to a selected ultrasonic energy frequency or frequency range. For example, an ultrasonic energy frequency range from about 25 kHz to about 29 kHz effectively debrides pathologic musculoskeletal tissue (e.g., scar tissue associated with a tendon) while reducing the likelihood of trauma to healthy soft tissue.

Figure 11:
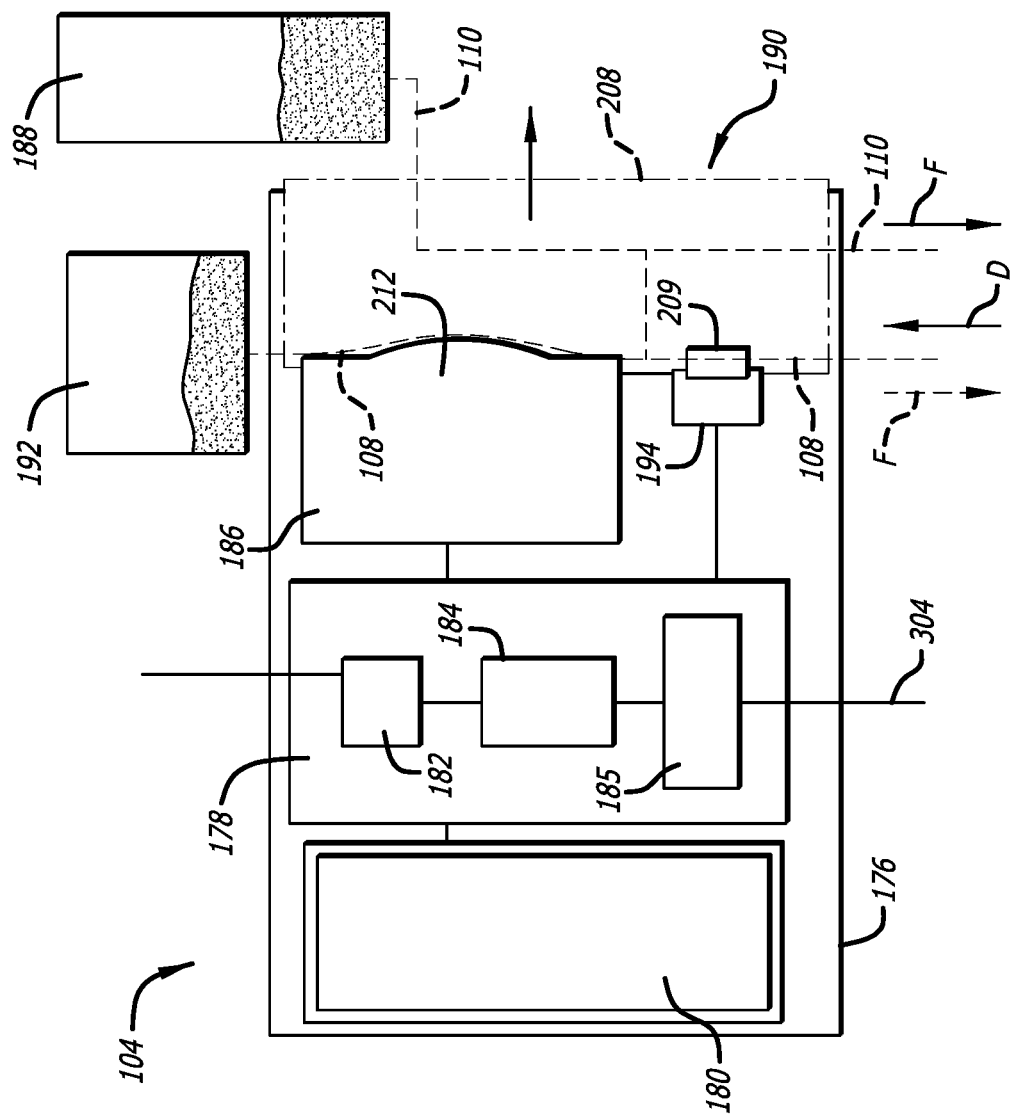
FIG. 11 is a schematic view of one example of the controller, illustrating the command module, the use interface and the tubing cassette.

As illustrated in FIGS. 1 and 11, in some embodiments, controller 104 may include: tubing cassette 190 and collector 192.

As illustrated in FIG. 11, controller 104 may include: (a) housing 176; (b) command module 178 including: (i) power source 182; (ii) processor 184; and (iii) signal filter 185; (c) vacuum source 186; (d) irrigation source 188; and (e) tubing cassette 190.

In some embodiments, command module 178 includes a main unit which preferably includes one or more processors electrically coupled by an address/data bus to one or more memory devices, other computer circuitry, and one or more interface circuits. The processor may be any suitable processor, such as a microprocessor from the INTEL PENTIUM® family of microprocessors. The memory preferably includes volatile memory and non-volatile memory. Preferably, the memory stores a software program that interacts with the other devices in system 100. This program may be executed by the processor in any suitable manner. In an example embodiment, the memory may be part of a "cloud" such that cloud computing may be utilized by system 100. The memory may also store digital data indicative of documents, files, programs, web pages, etc. retrieved from a computing device and/or loaded via an input device.

In some embodiments, command module 178 is configured to control flow from vacuum source 186.

In some embodiments, command module 178 is configured to control flow from irrigation source 188.

In some embodiments, command module 178 is configured to power delivery device 102.

In some embodiments, command module 178 is configured to, via user interface 180, enable a user to select instructions. In one embodiment, command module 178 is configured to, via user interface 180, provide instructions to a user via user interface 180.

In some embodiments, command module 178 includes signal filter 185 for delivering a conditioned power signal (e.g., a sinusoidal power signal at a selected amplitude and frequency) to delivery device 102.

As illustrated in FIG. 11, command module 178 may include at least one processor 184.

In some embodiments, controller 104 includes user interface 180. User interface 180 may include a touch screen system for controlling system 100.

In some embodiments, controller 104 includes power source 182. Power source 182 may include a battery, a capacitor, a transformer connected to an external power source, such as a wall socket, combinations thereof, or other means for providing electrical power to system 100. Power source 182 may also directly or indirectly deliver power to various components of controller 104 as appropriate.

In some embodiments, controller 104 includes vacuum source 186. In other embodiments, vacuum source 186 is external or separate from the controller. That is, vacuum source 186 is separate from and connected to controller 104. Vacuum source 186 may be a peristaltic pump.

In some embodiments, controller 104 includes collector 192. Collector 192 may be configured to receive detritus, fluid, or other matter being aspirated by the aspiration flow D. Collector 192 may be a bag or container. As illustrated in FIGS. 1 and 11, collector 192 may be separate from tubing cassette 190. In other embodiments, collector 192 may be maintained by, formed as a part of, or is a component within tubing cassette 190. In some embodiments, collector 192 may be configured to removeably connect to tubing cassette 190. In one embodiment, collector 192 is connected to the cassette 190 using double sided tape.

In some embodiments, controller 104 may include irrigation source 188. Irrigation source 188 may include a reservoir of irrigant (e.g., saline). In some embodiments, the reservoir is pressurized by gravity, a plunger (e.g., a syringe), or a pump (e.g., a peristaltic pump operated by controller 104 and optionally disposed within the housing 176) to generate fluid flow F. In other embodiments, irrigation source 188 is separate from system 100. In some of these embodiments, spike 113 may be configured to penetrate the separate irrigation source to supply fluid flow to system 100.

In one embodiment, controller 104 includes valve actuator 194. In one embodiment, valve actuator 194 is configured to direct fluid flow F into vacuum conduits of delivery device 102, for example for flushing purposes.

Figure 12:
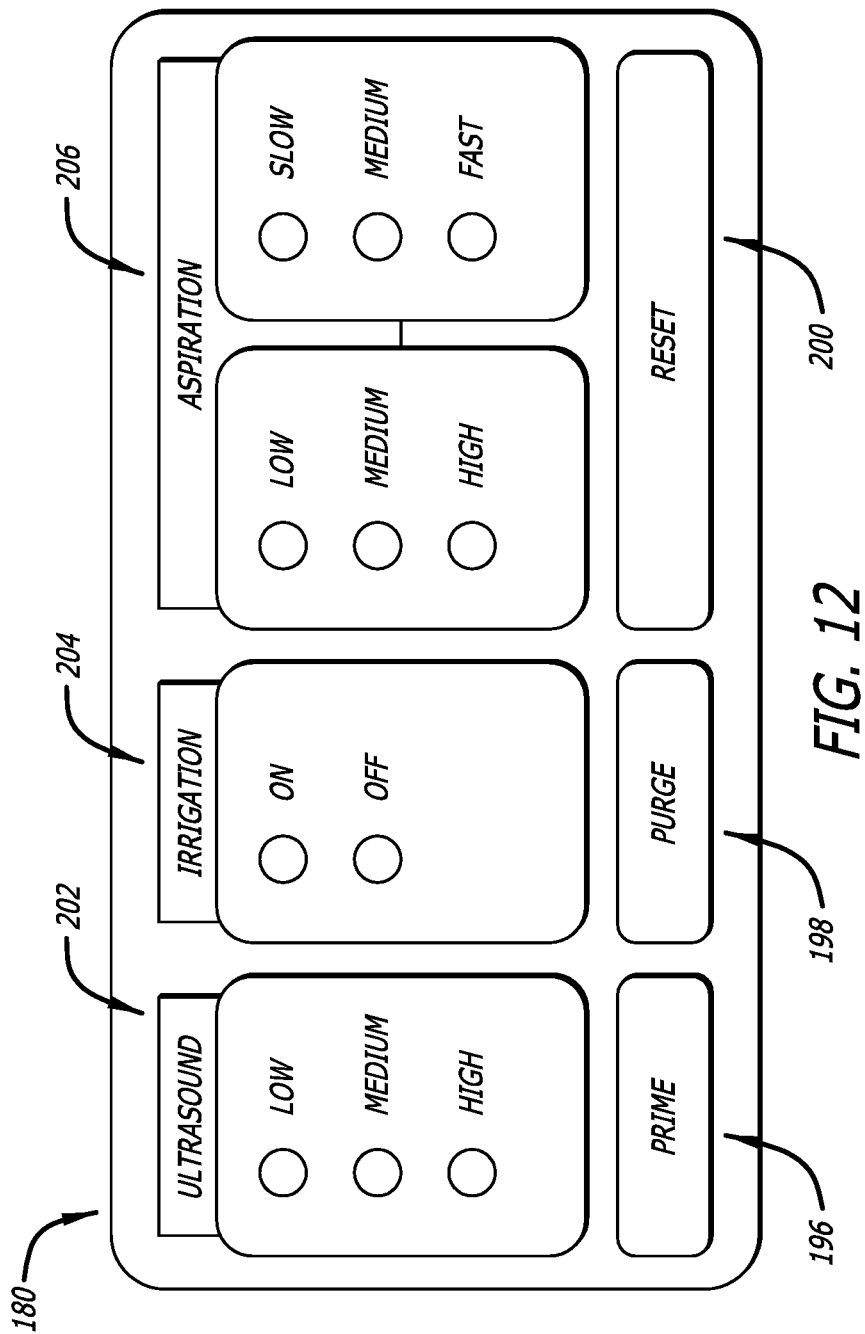
FIG. 12 is a schematic view of one example of the user interface of the controller.

Referring to FIG. 12, in some embodiments, user interface 180 includes: (a) prime phase button 196; (b) purge phase button 198; (c) and reset phase button 200. In some embodiments, user interface 180 enables a sequential operation of delivery device 102 starting with ultrasound level selection 202, irrigation level selection 204, and aspiration level selection 206, where a user is allowed to first select ultrasound level 202, then irrigation level 204, and finally aspiration level 206 in sequence when operating system 100. Selections 202, 204, 206 may be illuminated sequentially, first with ultrasound level selection 202, and a user may not be enabled to make a subsequent selection until the selection at hand has been made.

In some methods of operation, the ultrasound energy and irrigant, or fluid flow, are generally delivered concurrently, while aspiration flow is delivered intermittently. For example, the ultrasound energy and irrigant flow optionally cease during aspiration and are restarted once treatment is reinitiated. Alternatively, irrigant flow may cease and ultrasound energy continues during aspiration, although some of the beneficial effects from using irrigant during ultrasonic treatment (e.g., continuous tip cooling and tissue emulsification, as well as others) are potentially reduced by such operation.

In some embodiments, as illustrated in FIGS. 11 and 13A to 13C, tubing cassette 190 includes: (a) housing 208; (b) valve 209; (c) a portion of the vacuum line 108; (d) a portion of irrigation line 110 (designated by broken lines).

In some embodiments, vacuum line 108 and irrigation line 110 include a plurality of interconnected segments of medical tubing, although unitary constructs are a potential option as well.

Tubing cassette 190 may connect vacuum line 108 to vacuum source 186 in a relatively sterile manner. For example, where vacuum source 186 includes a peristaltic pump, tubing cassette 190 includes seat structure 210 for causing vacuum line 108 to engage pump drive 212 of vacuum source 186 that generates aspiration flow in vacuum line 108.

Figure 13A:
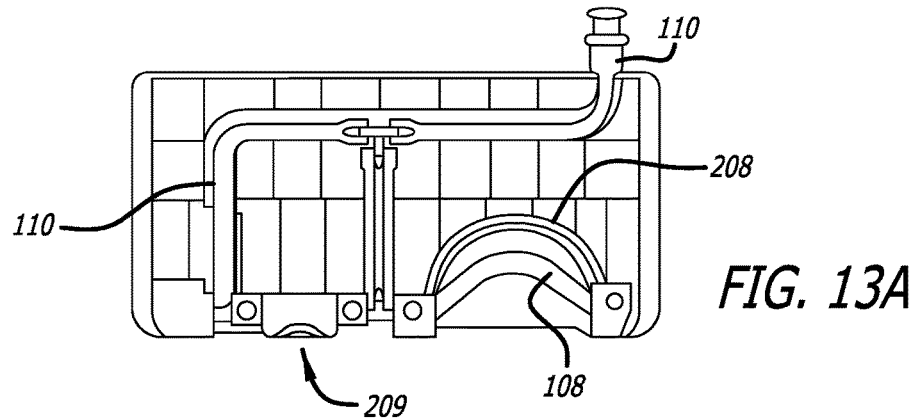
FIGS. 13A, 13B and 13C are alternative views of one example tubing cassette of the controller.
Figure 13B:
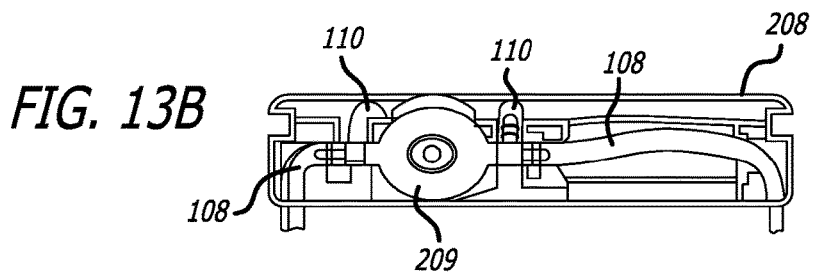
Figure 13C:
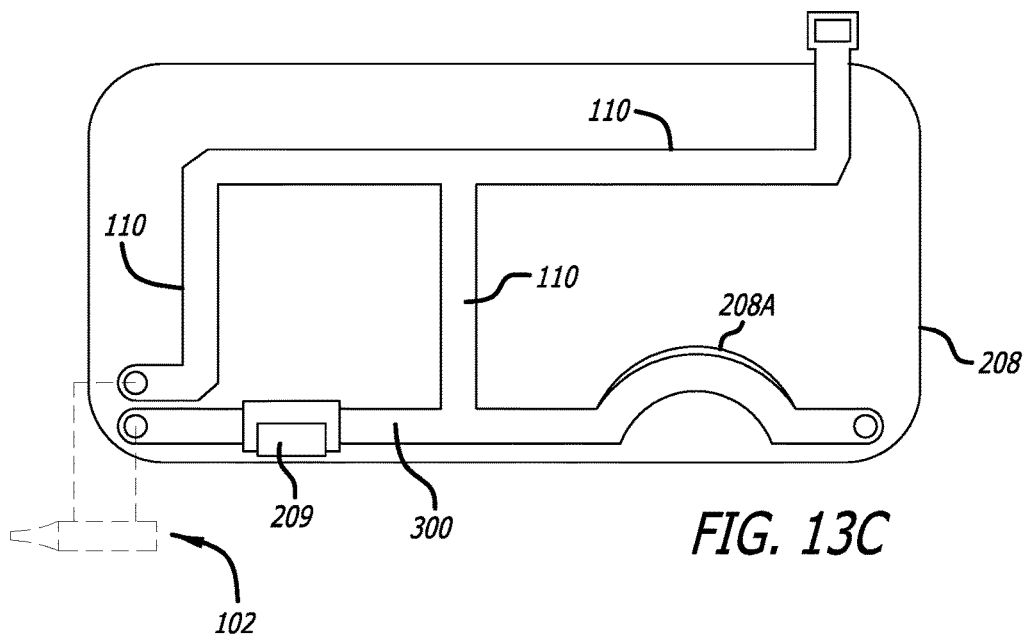

FIG. 13A illustrates an example interior side of tubing cassette 190 and FIG. 13B illustrates an example bottom side of tubing cassette 190. FIG. 13C is a schematic view of an example tubing cassette 190.

In some embodiments, vacuum line 108 and irrigation line 110 may be referred to as a tubing set.

In operation of one example embodiment, pump drive 212 of vacuum source 186 (e.g., a peristaltic pump) is received in seat structure 210 such that vacuum line 108 is engaged against seat structure 210 between the pump drive 212 and seat structure 210. Valve 209 is engaged by valve actuator 194 to press valve 209 closed such that flow from irrigation line 110 will not travel through vacuum line 108 to delivery device 102 (designated generally by a broken line rectangle in FIG. 7C). When vacuum line 108 is to be flushed, for example, valve 209 is released and fluid is able to flow into vacuum line 108 to the device and through the vacuum conduits. As previously referenced, the irrigant flowing through irrigation line 110 is optionally gravity pressurized or otherwise forced through system 100.

Assembly of system 100 includes remotely connecting delivery device 102 to controller 104, where controller 104 is a separate, remote module from delivery device 102. In other embodiments, delivery device 120 and controller 104, or portions thereof, are formed as a single unit.

In some embodiments, as illustrated in FIG. 1, controller 104 may include: (a) administration line 111; and (b) spike 113 which is operatively coupled to administration line 111.

In some embodiments, a plurality of disposable delivery devices similar to the delivery device 102 are provided with corresponding disposable cassettes, such as cassette 190 for each delivery device. Individually pre-tuning the devices to an appropriate ultrasonic energy frequency, such as that previously described, before delivery to the user removes a need to test and adjust power signal parameters or delivery device configurations prior to or during each procedure. Instead, in some embodiment, a single use cassette/delivery device kit is set up or configured prior to delivery to the end user, is then used in a treatment procedure, and is optionally discarded at the end of the procedure, thereby reducing operation time, a requisite skill level for "tuning" system 100, and/or additional components or systems for tuning delivery device 102. Moreover, the combination of cassette 190 and delivery device 102 eliminates a need to sterilize equipment before a procedure, as all components that come into contact with bodily fluids are pre-sterilized and discarded at the end of the procedure.

In some embodiments, system 100 is used in any of a variety of procedures.

In some embodiments, system 100 is used to perform an ultrasound-guided percutaneous tenotomy.

FIG. 14 illustrates a diagrammatic view of one example of system 100 being used in conjunction with ultrasound imaging system to deliver ultrasonic energy to a target musculoskeletal tissue site under ultrasonic imaging.

In operation, the tip portions of needle 136 and sleeve 117 may be percutaneously inserted without having to form an incision in the skin. That is, needle 136 and sleeve 117 may help facilitate atraumatic skin and soft tissue penetration without a need for a separate incision under ultrasonic imaging.

As shown in FIG. 14, advancement of the tip portions of needle 136 and sleeve 117 to target musculoskeletal tissue site 300 may be performed under guidance of ultrasound imaging system 302 including high-frequency ultrasound transducer 304 (e.g., a frequency greater than about ten MHz) and imaging device 306. Imaging system 302, in combination with the echogenic nature of tip portion of delivery device 102, permits intra-operative identification of target tissue site 300 in need of treatment and an ability to percutaneously deliver ultrasonic energy from the exposed portion of needle 136 to target tissue site 300.

Some methods of delivering ultrasonic energy to target tissue site 300 include connecting delivery device 102 to vacuum source 186, irrigation source 188, and power source 182 of controller 104 (directly or via the command module 178). Ultrasonic energy is generated by sending a power signal from command module 178 to the transducer. The ultrasonic energy is transmitted from the transducer to horn assembly 140 such that the exposed portion of needle 136 delivers ultrasonic energy at a frequency that is pre-selected to debride musculoskeletal tissue upon percutaneous insertion of needle 136 and sleeve 117 to target musculoskeletal tissue site 300.

In some embodiments, user interface 180 may be operated by a user to sequentially start up delivery device 102, including initiating ultrasonic energy delivery, irrigation flow to delivery device 102, and aspiration flow from delivery device 102. Once tissue treatment is completed, in some embodiments, tubing cassette 190 may be removed from controller 104, discarded, and replaced with a second, sterile tubing cassette (not shown) and is either pre-connected or subsequently connected to a second, sterile delivery device (not shown) to sterilize system 100 for a new procedure.

In some embodiments, target tissue site 300 includes pathologic tissues such as a region of scar tissue associated with tendon 308.

In some embodiments, the pathologic tissue is identified using high frequency ultrasonic imaging.

In some embodiments, needle 136 and sleeve 117 are delivered to target tissue site 300 under ultrasonic imaging, and ultrasonic energy is delivered through needle 136 to debride the musculoskeletal tissue (e.g., scar tissue) forming target tissue site 300.

In some embodiments, system 100 enables a user to identify target tissue site 300 entirely at the time of a procedure without cutting the skin of the patient.

As previously described, in some embodiments delivery device 102 is pre-tuned to deliver ultrasonic energy at a frequency that reduces the likelihood of trauma to healthy soft tissue while promoting debridement of the pathologic tissue. The percutaneous, minimally invasive nature of such a procedure facilitates access and treatment of such body tissue as part of an office-based procedure under local anesthesia.

In some embodiments, after the target tissue is treated and the needle and sleeve are removed from the patient, the patient may be discharged to home after a short period of in-office observation due to the minimally invasive nature of the procedure (e.g., as no local anesthesia would be necessary). For example, in similarly non-invasive procedures, post-procedure pain is typically variable, but often ranges from essentially no pain to moderately severe pain lasting less than seventy-two hours. Thus, various embodiments of system 100 provide for an office-based procedure under local anesthesia, thereby resulting in cost-savings to the patient by avoiding the costs of operating room time, where a patient may only need ice or cooling packs for analgesia and edema control after the treatment.

In some embodiments, after tissue treatment is completed, tubing cassette 190 may be removed from controller 104, discarded, and replaced with a second, sterile tubing cassette (not shown) and is either pre-connected or subsequently connected to a second, sterile delivery device (not shown) to sterilize the system 100 for a new procedure.

In some embodiments, a plurality of disposable delivery devices similar to the delivery device 102 are provided with corresponding disposable cassettes, such as cassette 190 for each delivery device. Individually pre-tuning the devices to an appropriate ultrasonic energy frequency, such as that previously described, before delivery to the user removes a need to test and adjust power signal parameters or delivery device configurations prior to or during each procedure. Instead, in some implementations, a single use cassette/delivery device kit is set up or configured prior to delivery to the end user, is then used in a treatment procedure, and is optionally discarded at the end of the procedure, thereby reducing operation time, a requisite skill level for "tuning" system 100, and/or additional components or systems for tuning the delivery device 102. Moreover, the combination of cassette 190 and delivery device 102 may eliminate a need to sterilize equipment before a procedure, as all components that come into contact with bodily fluids are pre-sterilized and discarded at the end of the procedure.

It should be appreciated that the system described herein is not limited to procedure described herein, and may be used in any suitable procedure. In some embodiments, the system described herein may be used as a phacoemulsification device. In some embodiments, the system described herein may be used to remove plaque in the heart, veins and/or arteries. In these such embodiments, needle 136 may have a length of about thirty-six inches.

Although the present disclosure has been described with reference to various examples, persons skilled in the art will recognize that changes may be made in form and detail without departing from the spirit and scope of invention. For example, various modifications and additions can be made to the exemplary embodiments discussed without departing from the scope of invention. While the embodiments described above refer to particular features, the scope of invention also includes embodiments having different combinations of features and embodiments that do not include all of the above described features.

The invention claimed is:

1. An ultrasonic energy delivery device configured to deliver ultrasonic energy to a musculoskeletal tissue site, the device comprising:
   a horn configured to receive energy generated by a transducer; and
   a work-hardened stainless steel needle brazed to the horn.

2. The device of claim 1 further comprising a processor configured to activate the transducer, wherein the processor includes stored instructions that when executed cause the device to deliver ultrasonic energy at a frequency selected to debride the musculoskeletal tissue.

3. The device of claim 1, wherein the stainless steel needle is a fully hardened hypodermic needle.

4. The device of claim 1, wherein the stainless steel needle is brazed to the horn using an alloy.

5. The device of claim 1, wherein the stainless steel needle is brazed to the horn using an acid flux.

6. The device of claim 1, wherein the stainless steel needle is brazed to the horn using an inert gas.

7. The device of claim 1, wherein the horn includes a tip portion that has an inwardly slanted portion configured to receive brazing material.

8. The device of claim 1, wherein the horn comprises stainless steel.

9. The device of claim 1, wherein the stainless steel needle brazed to the horn is not annealed during the brazing process.

10. A system configured to deliver ultrasonic energy to a musculoskeletal tissue site, the system comprising:
    a memory device containing instructions;
    a processor in communication with the memory device;
    a delivery device comprising:
      a horn; and
      a work-hardened stainless steel needle brazed to the horn;
    wherein execution of the instructions by the processor causes a transducer to generate ultrasonic energy at a pre-determined frequency suitable for debriding musculoskeletal tissue.

11. The system of claim 10 further comprising a fluid source, wherein the delivery device further comprises a fluid delivery conduit for delivering fluid from the fluid source to the musculoskeletal tissue site.

12. The system of claim 10, wherein the delivery device further comprises an aspiration conduit configured to remove detritus from the musculoskeletal site.

13. The system of claim 10, wherein the needle is brazed to the horn using an alloy.

14. The system of claim 10, wherein the needle is brazed to the horn using an acid flux.

15. The system of claim 10, wherein the needle is brazed to the horn using an inert gas.

16. The system of claim 10, wherein the delivery device includes a housing having a clear portion.

17. The system of claim 10, wherein the stainless steel needle is a fully hardened hypodermic needle.

18. The system of claim 10, wherein the stainless steel horn has a tip portion which has an inwardly slanted portion which is configured to receive brazing material.

19. The system of claim 10, wherein the stainless steel needle brazed to the stainless steel horn is not annealed during the brazing process.

* * * * *